(12) United States Patent
Hatfield et al.

(10) Patent No.: US 6,401,547 B1
(45) Date of Patent: Jun. 11, 2002

(54) DEVICE AND METHOD FOR MEASURING FLUID AND SOLUTE FLUXES IN FLOW SYSTEMS

(75) Inventors: Kirk Hatfield; P. Suresh C. Rao; Michael David Annable, all of Gainesville; Timothy J. Campbell, Parker, all of FL (US)

(73) Assignee: The University of Florida, Gainesville, FL (US)

( * ) Notice: Subject to any disclaimer, the term of this patent is extended or adjusted under 35 U.S.C. 154(b) by 0 days.

(21) Appl. No.: 09/430,607

(22) Filed: Oct. 29, 1999

(51) Int. Cl.[7] ............................. G01F 1/704; G01V 9/02

(52) U.S. Cl. .............................. 73/861.04; 73/863.23; 73/861.07; 73/64.56

(58) Field of Search .................. 73/861.04, 863.23, 73/861.07, 64.56, 863.41, 864.72

(56) References Cited

U.S. PATENT DOCUMENTS

| | | | | |
|---|---|---|---|---|
| 3,678,273 A | * | 7/1972 | Lewis | 250/303 |
| 3,993,131 A | | 11/1976 | Riedel | |
| 4,107,525 A | * | 8/1978 | Hart, Jr. | 250/303 |
| 4,167,870 A | * | 9/1979 | Haas | 73/861.04 |
| 4,484,626 A | | 11/1984 | Kerfoot et al. | |
| 5,077,471 A | | 12/1991 | Smith, Jr. et al. | |
| 5,339,694 A | | 8/1994 | Looney et al. | |
| 5,594,179 A | * | 1/1997 | Marsh | 73/861.078 |
| 5,821,864 A | | 10/1998 | Knop et al. | 73/49.2 X |
| 5,833,388 A | | 11/1998 | Edwards et al. | 405/52 |
| 5,942,103 A | | 8/1999 | Wang et al. | 205/787 |
| 5,942,440 A | | 8/1999 | Dooley et al. | 436/146 |
| 6,118,579 A | * | 9/2000 | Ipponmatsu et al. | 73/861.05 X |
| 6,182,505 B1 | * | 2/2001 | Segeral | 73/861.04 X |
| 6,284,219 B1 | * | 9/2001 | Ajami | 424/1.11 |

FOREIGN PATENT DOCUMENTS

| | | | | |
|---|---|---|---|---|
| DE | 42 30 919 A1 | | 3/1994 | |
| EP | 763731 A2 | * | 3/1997 | G01N/29/02 |
| GB | 2144214 A | * | 2/1985 | 250/428 |
| JP | 8-334396 | * | 12/1996 | G01F/1/704 |
| WO | 97/46853 | * | 12/1997 | G01F/1/64 |

OTHER PUBLICATIONS

Chapter 45 pp. 1055–1088 Water and Solute Flux; R. J. Wagenet, taken from a book entitled *Methods Of Soil Analysis*; Part 1, Physical and Mineralogical Methods; Second Edition; A. Klute, Editor, 1986 (copy enclosed) month not given.

Chapters 4, 9 and 10 from a book entitled *Practical Handbook of Ground–Water Monitoring*; edited by David M. Nielsen (copies enclosed). by Jan. 2000 pp. 97–141, 367–395 & 397–447.

*Journal of Hydrology*, Ion Exchange Resin Samplers For The In situ Measurement Of Major Cations In Soilwater Solute Flux; Elsevier Science Publishers, B.V. Amsterdam, 80 (1985) month not given pp. 325–335; R. W. Crabtree et al.

* cited by examiner

*Primary Examiner*—Thomas P. Noland
(74) *Attorney, Agent, or Firm*—McDonnell Boehnen Hulbert & Berghoff

(57) ABSTRACT

An improved method and apparatus for simultaneously monitoring the fluid flux, and the dissolved contaminants fluxes, in a flow field is provided comprising the use of a permeable unit containing an insoluble sorbent matrix that retains dissolved contaminants. The matrix may also contain tracers that can be displaced by the fluid flow. The method of monitoring comprises placing permeable units in contact with the contaminated flow field, thereby allowing contaminants to flow through the permeable unit and be sorbed on the insoluble sorbent matrix. Sufficient time is allowed for the contaminant concentrations in the flow field to reach equilibrium. The permeable unit is then removed from contact with the flow field and analyzed to determine cumulative contaminant fluxes and cumulative fluid fluxes.

1 Claim, 4 Drawing Sheets

SORBING MATRIX WITH TRACER

SORBING MATRIX

DISPLACED TRACER

DIRECTION OF FLUID FLOW

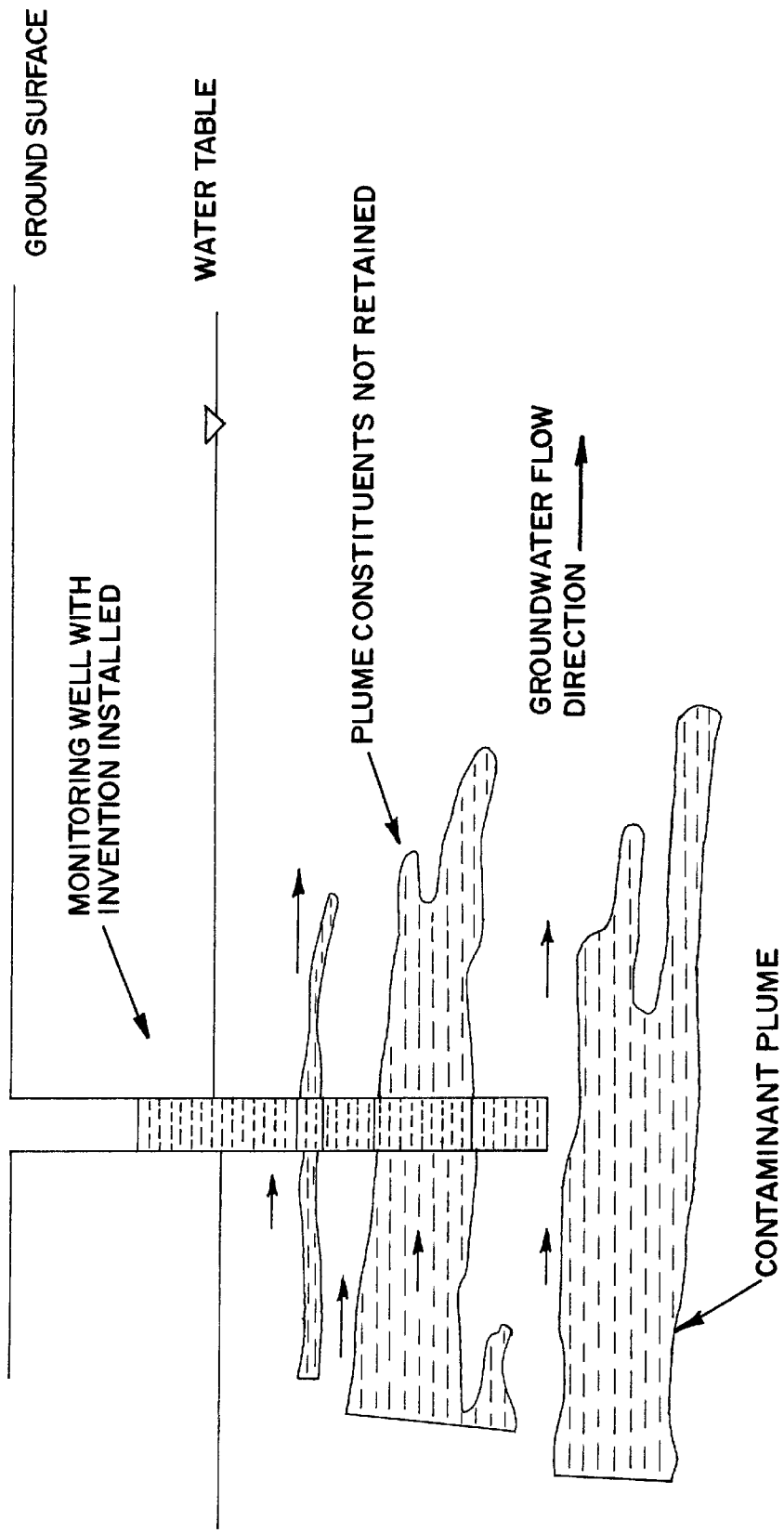

RELATIVE TRACER MASS RETAINED VERSES CUMLATIVE FLUID FLOW THROUGH THE FLUX METER

DEVICE AND METHOD FOR MEASURING FLUID AND SOLUTE FLUXES IN FLOW SYSTEMS

BACKGROUND OF THE INVENTION

1. Field of the Invention

The present invention generally relates to detection of organic and inorganic contaminants, and more particularly to the analysis of water supplies for the measurement and characterization of organic and inorganic contaminants therein. In particular, this invention relates to devices and methods for measuring cumulative dissolved solute fluxes and cumulative fluid fluxes in flow systems. The term flow systems as used herein includes, but is not limited to, saturated and variably saturated geologic and nongeologic media, such as saturated and unsaturated soils, sediments and aquifers.

2. Description of the Relevant Art

The presence of contaminants in ground water supplies and other water resources can present significant pollution problems. A wide variety of organic and inorganic contaminants may be present in subsurface, water-bearing geologic formations, depending on how the overlying land under consideration has been used. For example, many different organic solvents and related compounds (e.g., non-halogenated and halogenated organic compounds) may exist in groundwater supplies beneath factory sites and other locations where extensive use of these chemicals has occurred over long time periods or accidental spills or inappropriate disposal have occurred. Of particular concern are halogenated (e.g., chlorinated) solvents including perchloroethene (PCE), trichloroethene (TCE), dichloroethane (DCA), vinyl chloride (VC), methylene chloride (MC), and others. However, in addition to halogenated solvents, a wide variety of other organic compounds shall be encompassed within the term "organic contaminants" as discussed below. Of equal concern is the presence of benzene, toluene, xylenes, and other constituents of petroleum-based fuels (e.g., jet fuel, gasoline, diesel fuel, and the like) in waste-bearing geologic formations underlying various transportation-related facilities. Examples of such facilities include gasoline stations, airports, military bases, and the like. Other contaminants of various pesticides and nutrients used in crop production or suburban lawns and gardens or golf courses; and trace metals such as arsenic and chromium and the like used in industrial operations. At many sites, both organic and inorganic contaminants may be found as mixtures. A contaminant group designated as polyaromatic hydrocarbons (PAHs), such as naphthalene, phenanthene, anthracene, benzo-a-pyrene and others, are constituents of coal and/or tars and creosote found at former gas manufacturing sites and wood treating facilities. Regardless of the particular contaminants of concern, the presence of these chemicals at or near subsurface or surface water supplies is a considerable public health concern and of ecological significance. Accordingly, the present invention shall not be restricted to the monitoring of any given organic or inorganic compounds.

Several methods have been used to analyze water quality. Of particular importance is the analysis of groundwater existing in aquifers for concentrations of organic waste products. The term "aquifer" as used herein describes a large water-bearing geologic formation that is capable of yielding sufficient water to satisfy a particular demand (e.g., drinking water or industrial uses or irrigation needs). Prior testing methods have involved the drilling of wells directly into the aquifer, followed by the placement of screening materials within the wells. For deep aquifers, dedicated submersible pumps are then positioned in each well to withdraw numerous water samples of delivery to the well head. For shallow aquifers, bailing the water or pumping from above ground can be used for sampling. Thereafter, the samples are analyzed to determine the type and concentration of organic contaminants in the collected water samples. Measurement of water levels (or pressure) in a network of wells enables estimation of average fluid fluxes, if the hydraulic conductivity of transmitting of the aquifer is known.

While the prior methods provided important information regarding the levels of contamination in the water supplies of concern, they did not allow the estimation of contaminant fluxes and fluid flow fluxes. Although prior methods and apparatus are capable of measuring instantaneous fluid fluxes, no direct methods exist that permit simultaneous measurement of horizontal cumulative solute mass flux and the cumulative fluid flux in either saturated or variably saturated flow systems. Pan lysimeters (free drainage samplers) and suction lysimeters have both been used to measure cumulative fluid and dissolved solute fluxes when the direction of flow is vertical; however these technology are not suitable for measuring horizontal fluxes. Thus, to simultaneously measure cumulative fluid fluxes or cumulative dissolved solute fluxes in multiple directions associated with one or more fluids flowing in flow systems, a new method is needed.

Current methods for estimating contaminant mass flux (J) in aquifers are made from independent instantaneous measurements of flux (q) and solute concentration (C) in the pore water. Several methods exist for measuring q and C in saturated and unsaturated geologic formations. All existing methods are confined to providing estimates characterized over vertical or horizontal sampling lengths. For example, in cases of horizontal saturated flow, q and C are estimated over isolated vertical segments of a well; whereas, in estimating solute mass and fluid fluxes associated with vertical infiltration or leaching, the pertinent sampling lengths are the horizontal or areal extents of infiltration. Continuous temporal measurements of q can be done for saturated flow systems. Methods of measuring vertical unsaturated flow require that the flow be intercepted and then retained for direct volumetric measurement and chemical analysis. Thus, there is a method for estimating vertical cumulative water fluxes.

Solute concentrations (C) are usually measured at discrete moments in time in both saturated and unsaturated flow systems. No methods exist to measure cumulative solute fluxes for saturated flow systems. However, a device exists to intercept vertical unsaturated flow. Chemical analysis of the water intercepted by this device could be used to estimate cumulative dissolved solutes transported as a result of vertical fluid flow. Measured q and C are used as shown in the following equation to estimate the instantaneous contaminant flux, J.

$$J = qC \quad (1)$$

Equation (1) is assumed to characterize contaminant mass flux over a specified sampling dimensions (i.e., an isolated vertical segment of a monitoring well) and for a reported sampling time. For geologic media, this approach of characterizing contaminant fluxes is subject to significant experimental and conceptual errors. Consider first, that the specific discharge, q (the magnitude and the direction) and solute concentration, (C) are both functions of position and time.

This suggests that the magnitude and the direction of mass flux, J, also vary with position and time. Thus, any sampling of q and C over an isolated vertical or horizontal length precludes accurate local estimation of the magnitude and the direction of both fluid and contaminant fluxes. Second, the short-term sampling procedures often used to obtain C and q preclude estimation of the time-integrated (i.e., cumulative) values for fluid and contaminant fluxes. Such time-integrated contaminant fluxes are useful for assessing health risks associated with groundwater contamination, for assessing the direction and mass flow of contamination leaving a compliance boundary, for assessing the total amount of off-site contamination contributed by one or more sources, and for assessing the benefits of removing or remediating sources of subsurface contamination. Finally, because the above equation uses spatially-averaged values of q and C it does not produce valid estimates of contaminant fluxes in typically heterogeneous aquifers or vadose-zone flow systems. Accurate estimate of length-averaged contaminant fluxes, are obtained only from the direct spatial integration of measured local contaminant fluxes, J. Thus, existing methods for measuring q and C do not provide adequate discrete or time-integrated estimates of contaminant fluxes in saturated or variably saturated geologic formations.

Traditional testing methods also require a large amount of expensive equipment, are labor intensive, and involve complex operating procedures. Moreover, conventional monitoring techniques which require the removal of numerous fluid samples for individual testing typically generate large quantities of waste products (e.g., residual sample materials) which, if sufficiently contaminated, can present significant disposal problems. Prior to development of the present invention, a need therefore remained for an efficient testing system which avoids these disadvantages and enables ground water supplies (as well as surface water sources) to be tested in an accurate, rapid, and effective manner.

The claimed invention represents a unique and highly-efficient alternative to the methods listed above. It does not require extensive equipment (e.g., submersible pumps) and complex operating procedures. The invented device can be used to analyze large water supplies without extracting any contaminated liquid sample materials so that with disposal of generated waste fluids, problems are avoided. The invented device can be used to obtain continous estimates of the magnitude and direction of both fluid and dissolved solute fluxes over a specified sampling length (i.e. over an isolated section of monitoring well). Finally, the method and apparatus described below enable the water supply of interest to be simultaneously analyzed at multiple locations so that the contamination may be "mapped" enabling spatial delineation of the areas of concern. Decontamination of the water source can then occur in a more site-specific and accurate manner. The present invention therefore involves a highly effective testing system which represents a substantial advance in the art of contaminant detection and remediation as discussed further below.

SUMMARY OF INVENTION

It is an object of the present invention to provide a highly efficient testing method and apparatus which enables the quantitative and qualitative analysis of contaminants in a flow system.

It is another object of the invention to provide a method and a device for capturing a representative concentration of contaminants in a flow system which allows the analysis of a wide variety of different organic and inorganic materials at varying levels.

It is another object of the invention to provide a method and apparatus for monitoring contaminants in a flow system which uses an operating system and procedure of minimal complexity.

It is another object of the invention to provide a method and apparatus for monitoring contaminants in a flow system which avoids the need for pump systems.

It is a further object of the invention to provide a method and apparatus for monitoring contaminants in a flow system which enables testing to take place without physically removing any water samples from the test area.

It is an even further object of the invention to provide a method and apparatus for monitoring contaminants in water supplies which avoids the generation of waste products (e.g., residual sample materials), and likewise eliminates the disposal problems associated therewith.

Another object of the invention is to provide a method and apparatus for monitoring contaminants in a flow system which is characterized by reduced labor requirements and processing times.

It is a still further object of the invention to provide a method and apparatus for monitoring contaminants in water supplied which enables a spatial distribution (e.g., a vertical or horizontal analysis) of the contaminants to be obtained.

It is a still further object of the invention to provide a method and apparatus for monitoring fluids and contaminants and their associated local fluxes in water supplies which facilitates the mapping of contamination zones in a highly effective manner so that site-specific, high-efficiency remediation procedures may be initiated.

It is a still further object of the invention to provide a method and apparatus for monitoring fluids and contaminants and their associated local fluxes in water supplies to facilitate an assessment of the direction and mass flow of contamination leaving a compliance boundary.

It is a still further object of the invention to provide a method and apparatus for monitoring fluids and contaminants and their associated local fluxes in water supplies to facilitate an assessment of the total amount of off-site contamination contributed by one or more sources.

Another object of the invention is to provide a device and method for measuring the following at specific locations in a fluid flow system:

1) Directions and magnitudes of local cumulative fluxes of multiple fluid flows, and 2) Directions and magnitudes of local cumulative solute mass fluxes associated with these fluid flows.

Finally, another object of the invention is to provide a device and method of measuring the following at specific locations a flow system:

1) Directions and magnitudes of local cumulative water fluxes, and

2) Directions and magnitudes of local cumulative solute mass fluxes for solutes associated with the fluid flow.

In accordance with the foregoing, the invention involves both a system and a method that uses a permeable unit designed to simultaneously measure local cumulative dissolved solute fluxes and fluid fluxes when placed within a fluid flow system. As used herein, "fluid flow" can be, but is not limited to, groundwater or other fluids flowing in a porous medium such as a geologic formation (rock, soil, clay, and like materials). Typically, fluids within flow systems contain dissolved constituents, including organic and/or inorganic contaminants of concern.

The monitoring device of the present invention comprises a self-contained permeable unit that will intercept fluids and allow the fluids to flow through the unit, but not retain these fluids. The interior of the permeable unit contains at least one matrix of hydrophobic and hydrophilic permeable and insoluble sorbents that are capable of retaining dissolved organic and/or inorganic solutes present in fluid intercepted by the permeable unit. The sorbing matrix can also be impregnated with known amounts of fluid-soluble tracers; these tracers are used to estimate total fluid flux through the permeable unit. The selection of sorbent matrices to be used with the device could be, but need not be limited to porous pellets, fibers, or stabilized liquids or gels. The sorbent matrix or matrices that are packed within the permeable unit could have the inherent capacity to selectively sorb contaminants from the fluid flow or in the alternative, the matrix can be coated or impregnated with specific sorbents that are selected to absorb or adsorb specific contaminants.

BRIEF DESCRIPTION OF THE DRAWINGS

FIG. 3 is a cross-section view of a monitoring well containing the permeable unit in the path of groundwater flow.

DETAILED DESCRIPTION

Figure 1A:
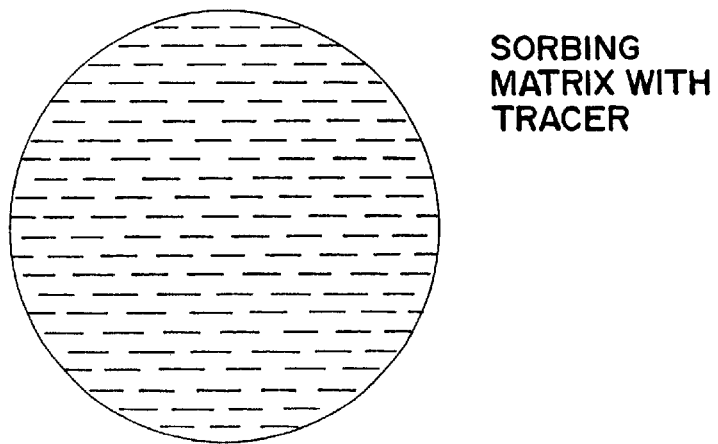
FIGS. 1A and 1B shows two cross-sections of a sorbent matrix containing a tracer before and after contact with a fluid flow containing contaminants.

The permeable unit of this invention contains at least one insoluble matrix of various hydrophobic and hydrophilic sorbents that have the property to selectively adsorb or absorb organic and inorganic solutes (i.e., contaminants) present in a fluid flowing through the device.

As used herein, "saturated flow" shall mean the flow of the mobile fluid of interest through a porous solid media with the total interconnected porosity or void volume of solid matrix filled with that fluid.

Likewise, "unsaturated flow" shall mean the flow of the mobile fluid of interest through a porous solid media in which a fraction of the total interconnected porosity of void volume of the solid media is filled with that fluid and the remaining fraction with another fluid or gas.

And finally, "variable saturated flow" describes the flow of the mobile fluid of interest through a porous solid media as varying in space and time from the extremes of saturated to unsaturated flow.

The matrix contains at least one sorbed resident tracer. The permeable unit may consist of a hollow tube with permeable walls or like structure suitable to hold the insoluble matrix. As stated, the insoluble matrix can take the form of particles, such as pellets, aggregates, spheres or other geometric forms. The permeable unit is designed so that it can be introduced and removed from a flow field, such as an access bore hole or monitoring well. For surface water flow systems, there is obviously no need for access holes, etc. The matrix must be insoluble when placed in the flow of the fluids of interest, and preferably is comprised of both adsorbents or ion exchange media. Adsorbents can be selected from aluminas, silicates, aluminosilicates (including molecular sieves), silica gel, magnesium or calcium silicate, clays, carbons and organic polymers. If the matrix comprises ion exchange media, it can comprise cation and anion exchangers, gel resins, phenolic resins, sulfonated phenolic resins, polymer cellulose composites and zeolites.

The accumulation of solutes on the insoluble sorbent matrix over a period of time represents the cumulative mass intercepted by the permeable unit, $M_s$. The mass flux is obtained as follows:

$$J = \frac{M_s}{t_d \cdot A_u} \qquad (2)$$

where, $t_d$ is the sampling time or the total time the unit resides in the flow field, and $A_u$ is an area normal to the direction of fluid flow that is used to define the fluid flux into the unit. For example, if the unit were being used in a monitoring well, of an aquifer, $A_u$ can be estimated by taking the product of the vertical sampling depth and the diameter of the unit. Corrections for diverging and converging flows into the device can be made to obtain an effective "sampling" diameter.

The solute mass retained on the sorbent matrix contained in the unit can be used to estimate cumulative solute fluxes into the permeable unit and time-average solute fluxes. These fluxes are valid over the dimensions of permeable unit contributing flow into the unit. For example, a permeable unit designed to sample the entire vertical depth of an aquifer could be used to characterize horizontal solute or groundwater contaminant fluxes continuously over the vertical extent of an aquifer. As described below, the horizontal magnitudes and directions of fluid flow into the permeable unit can be obtained.

Figure 1B:
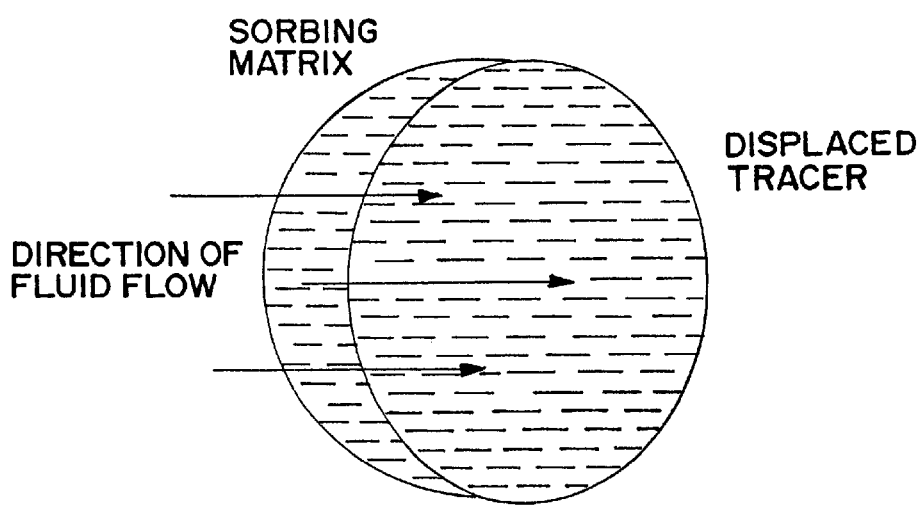

As mentioned, the insoluble sorbent matrix contained within the unit also is impregnated with known amounts of one or more resident fluid-soluble tracers. Preferably these resident tracers comprise organic and inorganic compounds with a range of partitioning characteristics. Examples of hydrophobic species which might be used as tracers include branched and straight-chain aliphatic hydrocarbons, aliphatic alcohols, aromatics and poly-aromatic hydrocarbons (PAHs), and non-ionic surfactants. Anionic tracers can include benzoates, benzenesulfonates, phenates, aliphatic carboxylic acids, and inorganics such as halides, nitrates, nitrites, sulfates, sulfites, phosphates, and metal oxides. Cationic tracers can include ammonium, organic amines, heterocyclic compounds, and inorganic metal ions. The tracers are selected based on the expected or known contaminants to be monitored and measured. For example, if perchloroethylene is known to be a contaminant, then a tracer selected from the group consisting of methyl-substituted alcohols such as methanol, 2-methyl-2-pentanol and 4,2-dimethyl-3 pentanol, would be used. Likewise, if chromate is known to be a contaminant, then a tracer selected from the group consisting of inorganic or organic anionic tracers is used. Alternatively, if nitrate is known to be a contaminant, bromide might be elected as a tracer used on an anion exchange resin media. These tracers are used to estimate total fluid flux and the primary directions of flow. As fluid flow, such as water containing contaminants, flows through the permeable unit, the contaminants will cause the soluble tracers to be leached from the sorbing matrix and lost from the permeable unit. FIG. 1 displays two hypothetical cross-sections of a unit configured as a circular column (such as one that could be installed in a monitoring well). FIG. 1A reveals a single tracer uniformly distributed over the cross-section of the matrix before any fluid has flowed through the unit. FIG. 1B reflects the subsequent spatial distribution of the tracer after exposure to a fluid flow field. Here, the tracer that has been displaced to the right and leached from the section in a manner consistent with the direction of fluid flow. The mass of tracer remaining within the sorbing matrix in FIG. 1B can be used to estimate the duration of exposure, the cumulative fluid volume intercepted by this section of the permeable unit.

Figure 2A:
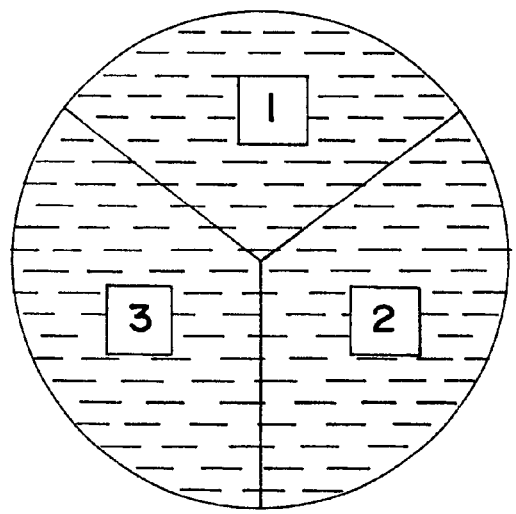
FIGS. 2A and 2B shows two cross-sections of a sorbent matrix containing three tracers before and after contact with a flow containing contaminants.
Figure 2B:
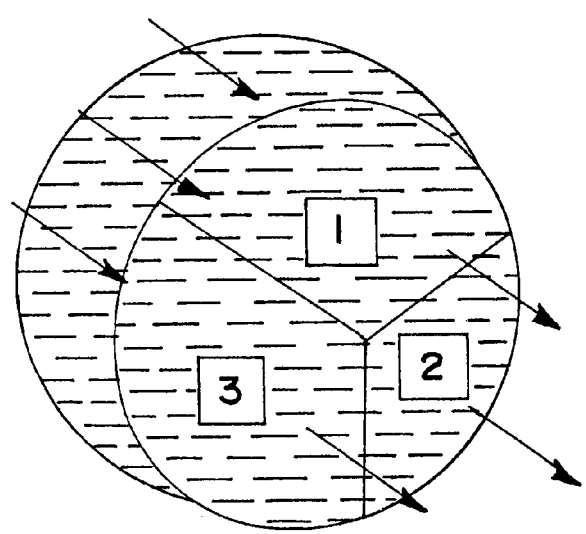

The direction of fluid flow through a section of the device can be obtained if at least three fluid-soluble tracers are used and their associated masses within the section determined after exposing the device to a flow field. FIG. 2 shows two hypothetical circular cross-sections of the device. Prior to any application, the initial spatial distribution of tracers 1, 2 and 3 is as illustrated where each occupies ⅓ of the sorbing matrix (see FIG. 2A). Flow as illustrated in FIG. 2B, causes tracer 2 to be lost more readily than 1 and 3. Similarly, if the flow direction were parallel to boundary defining interface between the initial distribution of tracers 1 and 2, then tracers 1 and 2 would be leached at the same rate. Such observations would change if the retardation factor, $R_d$ associated with any of the tracers were greater than one. The mass of each resident tracer retained after exposing the device to the fluid flow field is used to calculate the time-averaged or cumulative fluid flux intercepted by the device and the direction of the flux.

One significant potential application of the permeable unit will be the measurement of cumulative contaminant fluxes in aquifers. In this application a permeable unit filled with an insoluble sorbing matrix having one or more tracers impregnated thereon is lowered into a monitoring well located in an aquifer. Solutes from groundwater flowing through the well are retained on the sorbing matrix under natural and induced hydraulic gradients. The permeable unit is allowed to remain at a desired location within the aquifer for a fixed period of time, and then removed for laboratory analysis of adsorbed contaminants and the above described tracers to permit characterization (magnitude and direction) of both cumulative water flux and cumulative contaminant flux.

As a result of having groundwater flowing through the permeable unit over time, cumulative flows and the cumulative horizontal solute fluxes can be measured. For a unit designed to interrogate the entire vertical depth of an aquifer, the vertical distributions of tracer mass remaining in the device at various depths would yield a vertical characterization of the horizontal cumulative fluid flow distribution. In addition, this device would provide a vertical distribution of contaminant fluxes. FIG. 3 illustrates a device intercepting a fluid flow plume at various depths. The permeable unit is placed in a monitoring location, in any orientation (i.e., vertical, horizontal, etc.) depending on the flow system being monitored provided that the unit is placed in the flow system and subjected to fluid flux for a specific time period and then removed from the monitoring location. The matrix is then removed from the unit for analysis. The analysis involves segmenting the matrix, extracting the retained contaminants and remaining tracer(s), performing analysis of extracted materials and calculation of magnitudes and directions of cumulative or time-averaged fluid and dissolved solute fluxes. An analysis of the sorbent matrix would quantify vertical variations in the horizontal groundwater contaminant fluxes.

By installing several devices along a control plane situated perpendicular to the general groundwater flow direction (and this flow could be vertical or horizontal), it is possible to obtain local estimates of the cumulative contaminant mass flux across a control plane. In the case of saturated flow systems where the groundwater flow is generally horizontal, vertical characterization (cumulative and time-averaged magnitude and direction) of this flow and contaminant fluxes is possible by either installing several permeable units at specific depths or by installing a larger unit that can be segmented vertically.

One of the simplest permeable unit configurations is a circular column (such as one installed in a groundwater monitoring well). At a minimum, this unit would contain at least one insoluble sorbing matrix and having at least one tracer absorbed thereon which before installation, is uniformly distributed over the sorbing matrix as shown in FIG. 1 (see Section-A). Exposing the device to flowing groundwater for duration, $t_d$, leaches the tracer from the matrix and the unit and produces a residual distribution of tracer as shown in FIG. 1 (see Section B). The dimensionless relative mass, $M_R$, defined as the fraction of initial mass remaining of tracer remaining, within the circular cross-section of the matrix is given by the following equation:

$$M_R = \frac{2}{\pi}[\arcsin\beta - \xi\beta] \quad (3)$$

in which, $$\beta = \sqrt{1 - \xi^2} \quad (4)$$

$$\xi = \frac{t_d q}{2R\Theta R_d} \quad (5)$$

$$R_d = 1 + \frac{\rho K_d}{\beta} \quad (6)$$

Here R is the radius of the sorbing matrix; $\Theta$ is the fluid content of the sorbing matrix, $t_d$ is the sampling duration or the time used to measure fluxes with the permeable unit; $\xi$ is the dimensionless cumulative volume of fluid conveyed through the unit and is closely related to the number of fluid pore volumes conveyed through the unit; $R_d$ is the tracer retardation factor for the sorbent(s) used in the unit; $\rho$=the bulk density of the sorbent; $K_d$=the tracer sorbent/water partition coefficient; and all other parameters are as previously defined. Equation (3) is valid for all sampling durations that fall within interval of $0 \leq t_d \leq 2R\Theta R_d/q$.

Figure 4:
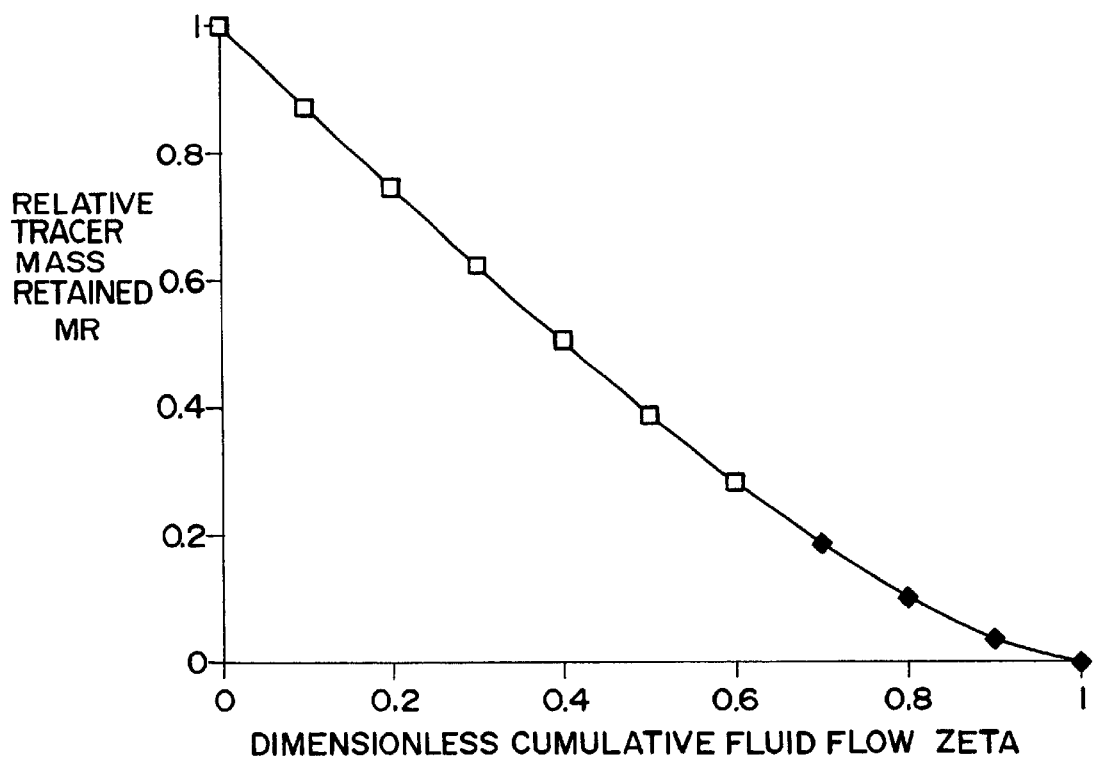
FIG. 4 is a generalized graph of relative tracer mass retained on a circular shaped sorbent matrix as a function of cumulative fluid flow through the permeable unit.

FIG. 4 shows a generalized plot of relative tracer mass $M_R$ retained on the sorbent in a circular device as a function of $\xi$, the dimensionless cumulative fluid volumes delivered through the unit. This plot was generated using equation (3). FIG. 4 clearly shows that equation (3) is linear for dimensionless flow volumes that are less than 0.6. Using this observation the relative mass of retained tracer can be expressed as:

$$M_R = 1 - k\xi \quad (7)$$

where k is 1.197.

Thus, equation (7) and (5) can be combined to give the following simple equation for estimating the time-averaged specific discharge, q, for fluid flow through the unit based on an analysis of the relative tracer mass retained on the insoluble sorbent matrix.

$$q = \frac{(1 - M_R)2R\Theta R_d}{kt_d} \quad (8)$$

Equation (1) can always be used regardless of $M_R$; however, equations 7 and 8 is essentially valid for situations where $M_R \geq 0.3$ or when less than 70 percent of the tracer has been leached from the device.

The determination of the horizontal direction of fluid flow is estimated using three or more tracers as shown in FIG. 2. Here, the relative mass of each tracer retained on the sorbing matrix is used to identify the time averaged or cumulative horizontal vectors of fluid flow.

Applications of the invention to unsaturated flow system is particularly pertinent where the objective is to estimate infiltration or to estimate apparent vertical contaminant (i.e., nutrient, pesticides and metals) transport velocities and fluxes. The purpose of using the permeable unit would be to characterize variations of vertical infiltration and solute fluxes over a horizontal subsurface compliance plane. To characterize infiltration or contaminant fluxes over a large area, multiple devices would be installed over a horizontal plane located at one or more depths beneath the ground surface.

As previously discussed, the present invention offers numerous benefits and advantages including (1) the simultaneous measurement of both fluid and solute cumulative fluxes; (2) the simultaneous long-term measurement of both fluid and solute cumulative fluxes (3) the rapid and efficient testing of water supplies using a minimal amount of energy, equipment, and process steps, with the elimination of complex procedures involving submersible pumps, (4) the ability to test a wide variety of water samples and supplied in situ for many different contaminants; (5) elimination of the need to physically withdraw multiple water samples at the test site which eliminates waste accumulation and disposal problems; (6) a high degree of portability which enables testing to occur at remote location without transporting large amounts of equipment; (7) a reduction in equipment , material, and personnel costs compared with traditional procedures; and (8) the ability to test a water supply at multiple locations in the supply which facilitates the production of a vertical and/or horizontal contaminant profile so that site-specific remediation can be achieved.

For these reasons, the claimed invention represents a significant advance in the art of pollution detection and control in fluid flow systems. Having herein set forth preferred embodiments of the invention, it is anticipated that suitable modifications may be made thereto by individuals skilled in the art which nonetheless remain within the scope of the invention. For example, the invention shall not be limited to any size or shape parameters, analytical equipment, hardware, and other similar items. In this regard, the present invention shall only be construed in accordance with the following claims.

We claim:

1. A method of estimating simultaneously the magnitude and direction of cumulative and time-average fluid flux and dissolved solute mass flux within a flow system comprising, providing at least one permeable unit containing at least one insoluble sorbent matrix and at least one resident tracer sorbed on sorbent thereof;

introducing the permeable unit into a flow system having fluid flux containing contaminants;

allowing the fluid flux to contact the sorbent matric;

recording the time that the sorbent matrix is in contact with the fluid flux;

removing the permeable unit from the flow system;

removing the sorbent matrix from the permeable unit for analysis; and analyzing the sorbent matrix to quantify the cumulative fluid flux from the mass of resident tracer remaining on the sorbent and to determine contaminant identification, concentration and flux.

* * * * *